(12) United States Patent
Kesten et al.

(10) Patent No.: US 7,122,019 B1
(45) Date of Patent: Oct. 17, 2006

(54) INTRA-AORTIC RENAL DRUG DELIVERY CATHETER

(75) Inventors: Randy J. Kesten, Mountain View, CA (US); Michael H. Rosenthal, Palo Alto, CA (US); Sam G. Payne, Santa Clara, CA (US); Andrew K. Kramer, Los Gatos, CA (US); Sophia Pesotchinsky, Los Altos, CA (US)

(73) Assignee: Flowmedica Inc., Fremont, CA (US)

(*) Notice: Subject to any disclaimer, the term of this patent is extended or adjusted under 35 U.S.C. 154(b) by 544 days.

(21) Appl. No.: 09/724,691

(22) Filed: Nov. 28, 2000

(51) Int. Cl.
*A61M 31/00* (2006.01)
*A61M 29/00* (2006.01)
*A61M 37/00* (2006.01)
*A61N 1/362* (2006.01)

(52) U.S. Cl. ................ 604/93.01; 604/96.01; 604/509; 604/284; 604/103.07; 604/101.03; 604/6.16; 600/16; 600/17

(58) Field of Classification Search ... 604/93.01–96.01, 604/509, 284, 103.7, 919, 101.03, 914, 6.16, 604/97.01, 508–500, 527, 104, 102, 271, 604/96, 103; 600/16–17, 1, 13; 606/194, 606/192; 623/1.11–1.15
See application file for complete search history.

(56) References Cited

U.S. PATENT DOCUMENTS 2,499,045 A 2/1950 Walker et al.
3,455,298 A 7/1969 Anstadt (Continued)

FOREIGN PATENT DOCUMENTS

DE 43 24 637 A1 7/1993
EP 0 654 283 A1 11/1994

(Continued)

OTHER PUBLICATIONS

Fox, S.L.; "Mechanisms of Contraction," Human Physiology, Fourth Edition, pp;. 300–323.

(Continued)

*Primary Examiner*—Brian L. Casler
*Assistant Examiner*—Roz Maiorino
(74) *Attorney, Agent, or Firm*—John P. O'Banion; James C. Peacock, III (57) ABSTRACT

A catheter for delivering a therapeutic or diagnostic agent to a branch blood vessel of a major blood vessel, generally comprising an elongated shaft having at least one lumen in fluid communication with an agent delivery port in a distal section of the shaft, an expandable tubular member on the distal section of the shaft, and a radially expandable member on the tubular member. The tubular member is configured to extend within the blood vessel up-stream and down-stream of a branch vessel, and has an interior passageway which is radially expandable within the blood vessel to separate blood flow through the blood vessel into an outer blood flow stream exterior to the tubular member and an inner blood flow stream within the interior passageway of the tubular member. The radially expandable member is located down-stream of the shaft agent delivery port, and has an expanded configuration with an outer diameter larger than an outer diameter of the tubular member. The expanded radially expandable member is configured to decrease the blood flow in the outer blood flow stream down-stream of the branch vessel. The catheter provides for delivery of an agent to a branch vessel of a major vessel, and continuous perfusion of the major blood vessel. Another aspect of the invention is directed to methods of delivering a therapeutic or diagnostic agent to one or both kidney's of a patient.

14 Claims, 8 Drawing Sheets

U.S. PATENT DOCUMENTS

| | | |
|---|---|---|
| 3,516,408 A | 6/1970 | Montanti |
| 3,667,069 A | 6/1972 | Blackshear et al. |
| 3,730,186 A | 5/1973 | Edmunds, Jr. et al. |
| 3,791,374 A | 2/1974 | Guarino |
| 3,995,623 A | 12/1976 | Blake et al. |
| 4,309,994 A | 1/1982 | Grunwald |
| 4,345,602 A | 8/1982 | Yoshimura et al. |
| 4,407,271 A | 10/1983 | Schiff |
| 4,423,725 A | 1/1984 | Baran et al. |
| 4,459,977 A | 7/1984 | Pizon et al. |
| 4,490,374 A | 12/1984 | Bandurco et al. |
| 4,493,697 A | 1/1985 | Krause et al. |
| 4,536,893 A | 8/1985 | Parravicini |
| 4,546,759 A | 10/1985 | Solar |
| 4,554,284 A | 11/1985 | Stringer et al. |
| 4,685,446 A | 8/1987 | Choy |
| 4,705,502 A | 11/1987 | Patel |
| 4,705,507 A | 11/1987 | Boyles |
| 4,712,551 A | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,817,586 A | 4/1989 | Wampler |
| 4,834,707 A | 5/1989 | Evans |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A | 7/1990 | Jarvik |
| 4,950,226 A | 8/1990 | Barron |
| 4,957,477 A | 9/1990 | Lundback |
| 4,964,864 A | 10/1990 | Summers et al. |
| 4,976,691 A | 12/1990 | Sahota |
| 4,976,692 A | 12/1990 | Atad |
| 4,990,139 A | 2/1991 | Jang |
| 4,995,864 A | 2/1991 | Bartholomew et al. |
| 5,002,531 A | 3/1991 | Bonzel ........................ 604/96 |
| 5,053,023 A | 10/1991 | Martin |
| 5,059,178 A | 10/1991 | Ya |
| 5,067,960 A | 11/1991 | Grandjean |
| 5,069,680 A | 12/1991 | Grandjean |
| 5,073,094 A | 12/1991 | Dorman et al. |
| 5,089,019 A | 2/1992 | Grandjean |
| 5,098,370 A | 3/1992 | Rahat et al. |
| 5,098,442 A | 3/1992 | Grandjean |
| 5,112,301 A | 5/1992 | FEnton, Jr. et al. |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,163,910 A | 11/1992 | Schwartz et al. |
| 5,167,628 A | 12/1992 | Boyles |
| 5,180,364 A | 1/1993 | Ginsburg |
| 5,205,810 A | 4/1993 | Guiraudon et al. |
| 5,226,888 A | 7/1993 | Arney |
| 5,256,141 A | 10/1993 | Gencheff et al. |
| 5,257,974 A * | 11/1993 | Cox ...................... 604/103.05 |
| 5,282,784 A | 2/1994 | Willard |
| 5,290,227 A | 3/1994 | Pasque |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,358,519 A | 10/1994 | Grandjean |
| 5,364,337 A | 11/1994 | Guiraudon et al. |
| 5,383,840 A | 1/1995 | Heilman et al. |
| 5,397,307 A | 3/1995 | Goodin |
| 5,429,584 A | 7/1995 | Chiu |
| 5,453,084 A | 9/1995 | Moses |
| 5,464,449 A | 11/1995 | Ryan et al. |
| 5,484,385 A | 1/1996 | Rishton |
| 5,505,701 A | 4/1996 | Anaya Fernandez de Lomana ................ 604/99 |
| 5,509,428 A | 4/1996 | Dunlop |
| 5,558,617 A | 9/1996 | Heilman et al. |
| 5,599,306 A * | 2/1997 | Klein et al. ............ 604/103.01 |
| 5,609,628 A | 3/1997 | Keranen |
| 5,617,878 A | 4/1997 | Taheri |
| 5,643,171 A | 7/1997 | Bradshaw et al. |
| 5,643,215 A | 7/1997 | Fuhrman et al. |
| 5,702,343 A | 12/1997 | Alferness |
| 5,713,860 A * | 2/1998 | Kaplan et al. ......... 604/103.01 |
| 5,720,735 A | 2/1998 | Dorros |
| 5,755,779 A | 5/1998 | Horiguchi |
| 5,762,599 A | 6/1998 | Sohn |
| 5,776,190 A | 7/1998 | Jarvik |
| 5,797,876 A | 8/1998 | Spears et al. |
| 5,902,229 A | 5/1999 | Tsitllik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,971,910 A | 10/1999 | Tsitlik et al. |
| 5,984,955 A | 11/1999 | Wisselink |
| 6,039,721 A * | 3/2000 | Johnson et al. .............. 604/508 |
| 6,077,256 A | 6/2000 | Mann |
| 6,086,527 A | 7/2000 | Talpade |
| 6,117,117 A | 9/2000 | Mauch |
| 6,165,120 A | 12/2000 | Schweich, Jr. et al. |
| 6,287,608 B1 | 9/2001 | Levin et al. |

FOREIGN PATENT DOCUMENTS

| | | |
|---|---|---|
| EP | 0 884 064 A2 | 5/1998 |
| WO | WO 98/03213 | 1/1998 |
| WO | WO 98/17347 | 4/1998 |
| WO | WO 98/52639 | 11/1998 |
| WO | WO 99/33407 | 12/1998 |
| WO | WO 99/22784 | 5/1999 |
| WO | WO 99/51286 | 10/1999 |
| WO | WO 00/41612 | 1/2000 |
| WO | WO 01/41861 | 6/2001 |

OTHER PUBLICATIONS

Cohn, Jay N.; "The Management of Chronic Heart Failure," The New England Journal of Medicine, pp. 490–498, Aug. 15, 1996.

Levin, Howard, R. et al.; "Reversal of Chronic Ventricular Dilation in Patients with End–Stage Cardiomyopathy by Prolonged Mechanical Unloading," vol. 91, No. 11, pp. 2727–2748, Jun. 1, 1995.

Linden, R.J. et al.; "The Nature of the Atrial Receptors Responsible for a Reflex Decrease in Activity in Renal Nerves of the Dog," The Physiological Society, pp. 31–40, (1980).

Katsumata et al.; "Newly–Developed Catheter for Cardio–Renal Assist During Intraaortic Balloon Counterpulsation," The Japanese Journal of Thoracic Surgery, vol. 46, pp. 767–770, (1993).

Kehrer et al.; "Construction and Experimental Application of a Catheter for Selective Arterial Kidney Perfusion in Situ," Urological Research, vol. 13, pp. 85–89, (1985).

"FDA Form 510(K) on Related Correspondence for Advanced Equipment Development, Inc."

Garwood, Susan et al.; "Renal Preservation Strategies for High Risk Patients," University of Chico School of Medicine, Cover Page, Table of Contents Page, pp. 1–19, (1998).

Postman, C.T. et al.; "Treatment of Renal Artery Stenosis with Intra–Arterial Stents," Ned Tijdshr Genneeskd., vol. 142, No. 39, pp. 2132–2137, Sep. 26, 1998. Abstract Only.

Jacobs, M.J. et al.; "Reduced Renal Failure Following Thoracoabdominal Aortic Aneurysm Repair by Selective Prefusion," Eur. J. Cardiothorac. Surg., vol. 14, No. 2, pp. 201–205, Aug. 1998. Abstract Only.

Novick, A.C.; "Atherosclerotic Ischemic Nephropathy. Epidemiology and Clinical Considerations," Urol. Clin. North Am., vol. 21, No. 2, pp. 195–200, May, 1994. Abstract Only.

Canaud, B. et al.; "Temporary Vascular Access for Extracorporeal Renal Replacement Therapies in Acute Renal Failure Patients," Kidney Int. Suppl., vol. 66, pp. S142–S150, May, 1998. Abstract Only.

Iannone, L.D. et al.; "Effect of Primary Balloon Expandable Renal Artery Stents on Long–Term Patency, Renal Function, and Blood Pressure in Hypertensive and Renal Insufficient Patients with Renal Artery Stenosis," Cathet. Cardiovasc. Diagn., vol. 37, No. 3, pp. 243–250, Mar., 1996. Abstract Only.

White, C.J. et al.; "Renal Artery Stent Placement: Utility in Lesions Difficult to Reat with Balloon Angioplasty," Am. Coll. Cardiol., vol. 30, No. 6, pp. 1445–1450, Nov. 15, 1997. Abstract Only.

Bergey, E.A. et al.; "Transhepatic Insertion of Vascular Dialysis Catheters in Children: A Safe, Life–Prolonging Procedure," Pediatr. Radiol., vol. 29, No. 1, pp. 42–50, Jan. 1999. Abstract Only.

Masaki, Z. et al.; "In Situ Perfusion by Retrograde Cannulation of a Tumor Artery for Nephron–Sparing Surgery," Int. J. Urol, vol. 2, No. 3, pp. 161–165, Jul., 1995. Abstract Only.

Walker, H.S. et al.; "Use of a Balloon–Tipped Perfusion Catheter for Renal Preservation During Suprarenal Abdominal Aortic Operations," J. Vasc. Surg., vol. 2, No. 2, pp. 337–339, Mar., 1985. Abstract Only.

Seiter, H. et al.; "Modified T–Catheter and its use for Transvenous Hypothermic in Situ Perfusion in the Surgical Restoration of the Kidney with *Staghorn calculi*," Z. Urol Nephrol., vol. 76, No. 6, pp. 403–406, Jun., 1983. Abstract Only.

Eisenberger, F. et al.; "Transfemoral Cannulation of the Renal Vessels. Diagnostic and Therapeutic use in Urology," Urologe [A], vol. 16, No. 1, pp. 1–5, Jan., 1977. Abstract Only.

Bischoff, W. et al.; "Modified in Situ Perfusion of the Kidney Using Balloon Catheters," vol. 94, No. 30, pp. 1695–1697, Oct. 21, 1976. Abstract Only.

Kehrer, G. et al.; "Construction and Experimental Application of a Catheter for Selective Arterial Kidney Perfusion in Situ," Urol. Res., vol. 13, No. 2, pp. 85–89, (1985). Abstract Only.

Williams, D.M. et al.; "Design and Testing of a High–FLo2 Autoperfusion Catheter: An Experimental Study," J. Vasc. Interv. Radiol., vol. 3, No. 2, pp. 285–290, May, 1992. Abstract Only.

Kobayashi, A. et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682–684, May 25, 1992. Abstract Only.

Greco, B.A. et al.; "Atherosclerotic Ischemic Renal Disease," Am. J. Kidney Dis., vol. 29, No. 2, pp. 167–187, Feb., 1997. Abstract Only.

Middleton, J.P.; "Ischemic Disease of the Kidney: How and Why to Consider Revascularization," J. Nephrol., vol. 11, No. 3, pp. 123–136, May–Jun., 1998. Abstract Only.

Katsumata, T. et al.; "Newly–Developed Catheter for Cardio–Renmal Assist During Intraaortic Balloon Counterpulsation," Kyobu Geka, vol. 46, No. 9, pp. 767–770, Aug., 1993. Abstract Only.

Akaba, N. et al.; "A Cylinder–Shaped Balloon Catheter for the Management of Dissecting Aneurysms in Acute Stage," Herz, vol. 17, No. 6, pp. 390–393, Dec., 1992. Abstract Only.

Mathis, J.M. et al.; "Use of Guide Catheter as a Temporary Stent During Microcatheter Intervention," AJNR Am. J. Neuroradiol, vol. 19, No. 5, pp. 932–933, May, 1998. Abstract Only.

* cited by examiner

INTRA-AORTIC RENAL DRUG DELIVERY CATHETER

BACKGROUND OF THE INVENTION

This invention relates to the field of medical devices, and more particularly to a catheter configured for drug delivery.

Acute renal failure ("ARF") is an abrupt decrease in the kidney's ability to excrete waste from a patient's blood. This change in kidney function may be attributable to many causes. A traumatic event, such as hemorrhage, gastrointestinal fluid loss, or renal fluid loss without proper fluid replacement may cause the patient to go into ARF. Patients may also become vulnerable to ARF after receiving anesthesia, surgery, or α-adrenergic agonists because of related systemic or renal vasoconstriction. Additionally, systemic vasodilation caused by anaphylaxis, and antihypertensive drugs, sepsis or drug overdose may also cause ARF because the body's natural defense is to shut down, i.e., vasoconstrict, non-essential organs such as the kidneys. Reduced cardiac output caused by cardiogenic shock, congestive heart failure, pericardial tamponade or massive pulmonary embolism creates an excess of fluid in the body, which can exacerbate congestive heart failure. For example, a reduction in blood flow and blood pressure in the kidneys due to reduced cardiac output can in turn result in the retention of excess fluid in the patient's body, leading, for example, to pulmonary and systemic edema.

Previously known methods of treating ARF, or of treating acute renal insufficiency associated with congestive heart failure ("CHF"), involve administering drugs. However, many of these drugs, when administered in systemic doses, have undesirable side effects. Additionally, many of these drugs would not be helpful in treating other causes of ARF. While a septic shock patient with profound systemic vasodilation often has concomitant severe renal vasoconstriction, administering vasodilators to dilate the renal artery to a patient suffering from systemic vasodilation would compound the vasodilation system wide. In addition, for patients with severe CHF (e.g., those awaiting heart transplant), mechanical methods, such as hemodialysis or left ventricular assist devices, may be implemented. Mechanical treatments, such as hemodialysis, however, generally have not been used for long-term management of CHF. Such mechanical treatments would also not be help for patients with strong hearts suffering from ARF.

Intra-aortic balloon pumps (IABPs) have been suggested for use in diverting blood flow into branch arteries. One such technique involves placing an IABP in the abdominal aorta so that the balloon is situated slightly below (proximal to) the branch arteries. The balloon is selectively inflated and deflated in a counterpulsation mode so that increased pressure distal to the balloon directs a greater portion of blood flow into the branch arteries. Although the IABP method of counterpulsation may be effective for increasing coronary perfusion, it would not extend well to the renal arteries.

It would be a significant advance to provide an intra-aortic catheter for improved delivery of agents to a branch vessel such as a renal artery.

SUMMARY OF THE INVENTION

The invention is directed to a catheter controlling the flow of blood in a major blood vessel to a branch blood vessel, and particularly for delivering a therapeutic or diagnostic agent to the branch blood vessel with the blood flow thereto. The catheter generally comprises an elongated shaft, an expandable tubular member on a distal section of the shaft, and a radially expandable member on the expandable tubular member. Preferably, the elongated shaft has at least one lumen in fluid communication with an agent delivery port in a distal section of the shaft. The expandable tubular member is configured to extend within a major blood vessel up-stream and down-stream of a branch vessel, and has an interior passageway which is radially expandable within the major blood vessel to separate blood flow through the major blood vessel into an outer blood flow stream exterior to the tubular member and an inner blood flow stream within the interior passageway of the tubular member. Thus, the expandable tubular member provides a perfusion passageway in the major blood vessel. The radially expandable member is located down-stream of the agent delivery port and is positioned down-stream of the branch artery, and has an expanded configuration with an outer diameter larger than an outer diameter of the expanded tubular member located up-stream thereto. In the expanded configuration, the radially expandable member is configured constrict blood flow past an outer surface of the radially expandable member and direct at least part of the blood flow in the outer blood flow stream into the branch vessel, which, consequently, decreases the blood flow in the outer blood flow stream downstream of the branch vessel. The catheter of the invention provides for delivery of an agent to a side branch vessel of a major vessel, and continuous perfusion of the major blood vessel. Another aspect of the invention is directed to methods of delivering a therapeutic or diagnostic agent to one or both kidney's of a patient.

The term proximal should be understood to mean locations on the catheter relatively closer to the operator during use of the catheter, and the term distal should be understood to mean locations on the catheter relatively further away from the operator during use of the catheter. The term up-stream should be understood to mean locations on the catheter relatively further upstream in the blood flow within the blood vessel, when the catheter is in place in the patient's blood vessel. The term down-stream should be understood to mean locations on the catheter relatively further downstream in the blood flow within the blood vessel, when the catheter is in place in the patient's blood vessel.

The tubular member interior passageway defines a perfusion or blood pass-through lumen. The interior passageway is radially expandable, so that the tubular member can be expanded from an unexpanded configuration providing a low profile for insertion and advancement of the catheter within the patient's blood vessel, to an expanded configuration providing a desired level of perfusion within the blood vessel. The expanded interior passageway of the tubular member is sufficiently large to avoid or limit detrimental effects of occluding the blood vessel, and specifically, in one embodiment, the effects of infrarenal aortic occlusion. However, in addition to the inner blood flow stream within the inner lumen of the tubular member, the tubular member has an outer diameter in the expanded configuration along at least a section thereof which is configured to allow for an outer blood flow stream exterior to the tubular member which is at least in part directed or flowing to the branch vessel. As a result, the catheter can be used to deliver an agent from the agent delivery port into the outer blood flow stream and to the patient's branch vessel.

The tubular member can be expanded by a variety of suitable methods. In one embodiment, the tubular member is self-expanding. For example, a radially collapsed tubular member is expanded by release of a radially compressive force, as for example, by removal of a sheath of guide catheter from around the tubular member. Similarly, a wound or folded tubular member is expanded by allowing the member to unwind or unfold into the expanded tubular configuration. In a presently preferred embodiment, the tubular member comprises a cylindrical inflatable member formed of a plurality of fluid-communicating wall chambers, which is inflated by directing inflation fluid into the wall chambers. In another embodiment, the tubular member has a braided structure, which is expanded by retracting a pull line to thereby shorten the length of the braided structure. In another embodiment, the tubular member is a balloon, which is expanded by directing inflation fluid into an wall chamber of the tubular member.

The radially expandable member is on a proximal or down-stream section of the tubular member, and is configured to restrict blood flow in the blood vessel. The radially expandable member has an expanded configuration with a larger outer diameter than the expanded tubular member. The radially expandable member may be a separate member secured to the tubular member as for example, where the radially expandable member is a balloon secured to an outer surface of a tubular member. Alternatively, the radially expandable member may be an integral part of the tubular member so that the tubular member and radially expandable member are a one-piece unit of the catheter, as for example, where the tubular member is a frame or braided structure having a sheath thereon and the radially expandable member is a radially enlarged section of the tubular member which expands as the tubular member expands, or where the tubular member is cone shaped and the radially expandable member is the largest diameter section of the cone shaped tubular member.

In the expanded configuration, the radially enlarged member is configured to decrease blood flow in the outer blood flow stream down-stream of the branch vessel. Thus, a relatively large concentration of agent is delivered into the branch vessel from the agent delivery port, in comparison to the amount of agent allowed to flow through the blood vessel down-stream of the branch vessel. In one embodiment, the radially expandable member has an expanded outer diameter configured to partially occlude, i.e., restrict but not completely block, the outer blood flow stream in the blood vessel. Thus, a portion of the outer blood flow through the blood vessel is allowed to flow around and down-stream of an outer surface of the radially expandable member. However, in an alternative embodiment, the radially expandable member has an outer diameter configured to contact a wall of the blood vessel and thereby occlude the outer blood flow stream in the blood vessel down-stream of the branch vessel.

Thus, the catheter of the invention separates the blood flow through the blood vessel into an outer blood flow stream directed in part into the branch vessel having a relatively high concentration of agent, and an inner blood flow stream. The end of the tubular member positioned up-stream of the branch vessel is located up-stream of agent delivery port in the shaft, so that the inner blood flow stream within the tubular member has a relatively low amount of or no agent. Moreover, with the radially expandable member in the expanded configuration, the blood flow exterior to the tubular member down-stream of the branch vessel is decreased in comparison to the blood flow stream exterior to the tubular member up-stream of the branch vessel. As a result, the amount of agent in the outer blood flow stream directed into the branch vessel is improved.

The catheter of the invention can be used to deliver a variety of therapeutic or diagnostic agents to the patient's blood vessel. In one embodiment, vasoactive and/or renal protective agents such as Papaverine, are delivered to the renal arteries for treatment of ARF and fluid overload. Other preferred agents include Calcium-channel blockers such as nifedipine or verapamil, and fenoldapam, a dopamine $DA_1$ agonist. The tubular member inner lumen providing a perfusion pathway allows the catheter to be in place in the patient's blood vessel for extended periods of treatment. The period of treatment will depend on the application and the agent, but is typically about 2 to about 72 hours, preferably about 4 to about 8 hours.

The catheter of the invention provides improved agent delivery to a branch vessel with continuous perfusion of the major blood vessel due to the relatively large perfusion lumen in the tubular member. Thus, possible detrimental effects of infrarenal aortic occlusion are reduced or prevented. Moreover, the catheter of the invention provides a relatively large concentration of agent to the renal arteries with little loss of blood flow through the aorta to the lower limbs. The catheter configured for intra-aortic delivery of an agent provides for relatively quick, intraluminal placement of the catheter. These and other advantages of the invention will become more apparent from the following detailed description of the invention and the accompanying exemplary drawings.

DETAILED DESCRIPTION OF THE INVENTION

Figure 1:
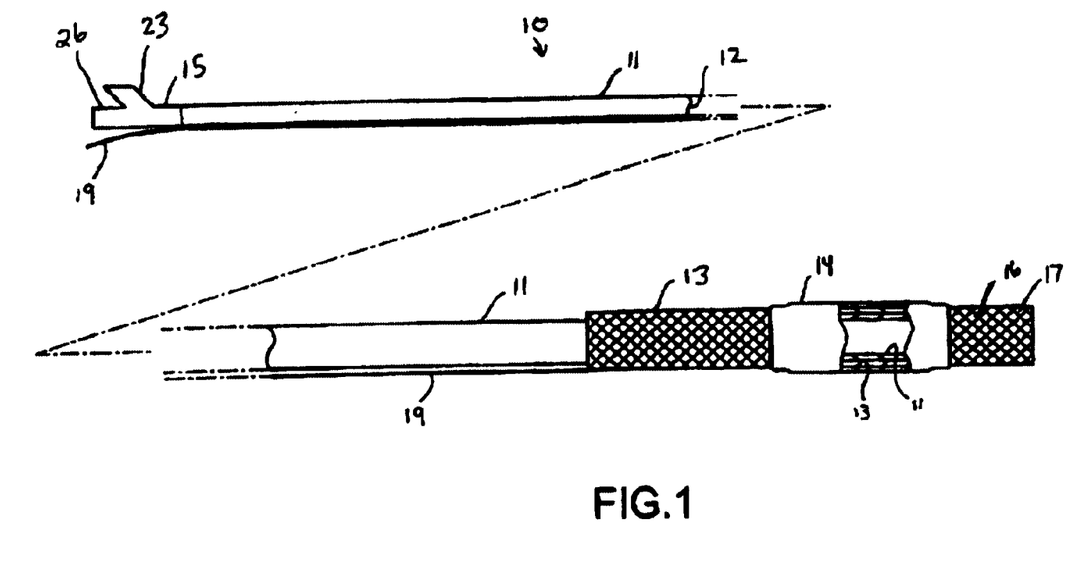
FIG. 1 is an elevational view, partially in section, of a catheter which embodies features of the invention, illustrating the expandable tubular member and balloon in an unexpanded configuration.

FIG. 1 illustrates a catheter 10 which embodies features of the invention, generally comprising an elongated shaft 11 having a proximal end, a distal end, and at least one lumen 12 extending therein, a tubular member 13 on a distal section of the catheter shaft 11 and a radially expandable member 14 on the tubular member 13. Adapter 15 on the proximal end of the shaft provides access to the catheter lumen. FIG. 1 illustrates the tubular member and the radially expandable member in low profile, unexpanded configurations for entry into the patient's blood vessel.

In the embodiment illustrated in FIG. 1, the radially expandable member 14 comprises an inflatable balloon. The balloon has proximal and distal ends secured to an outer surface of the tubular member 13, and an interior in fluid communication with an inflatable lumen 21 (FIG. 4) in the shaft 11. The balloon 14 can be formed of a variety of suitable materials typically used in the construction of catheter occlusion balloons, and in a presently preferred embodiment is highly compliant and is formed of a material such as latex, polyisoprene, polyurethane, a thermoplastic elastomer such as C-Flex. In alternative embodiment, the balloon may be noncompliant or semi-compliant. While discussed below primarily in terms of a radially expandable member comprising a balloon, it should be understood that the radially expandable member may have a variety of suitable configurations.

In the embodiment illustrated in FIG. 1, the tubular member 13 comprises braided filaments 16, such as wire, ribbon, and the like, having a sheath 17, and having a lumen or interior passageway 18 therein. A pull line 19 having a distal portion secured to the tubular member is configured to be retracted or pulled proximally to radially expand the tubular member 13. Specifically, the braided filaments 16 can reorient from a longer, smaller diameter configuration and a shorter, larger diameter configuration cause the tubular member to shorten, thereby radially expanding the tubular member 13. When the pull line is not under tension, the spring force of the elastomeric material of the sheath 17 will cause the tubular body defined by the braided filaments 16 to elongate and reduce in diameter. The sheath 17 is preferably an elastomeric polymer on the braided filaments. The sheath 17 can be on an inner or outer surface of the braided filaments, or the braided filaments can be completely or partially embedded within the sheath 17. In the embodiment in which the sheath is on a surface of the filaments, the sheath is preferably secured to a surface of the filaments as for example with adhesive or heat bonding. The braided filaments 16 can be formed of a variety of suitable materials such as metals or stiff polymers. A variety of suitable polymeric materials can be used to form the sheath 17. While discussed below primarily in terms of a tubular member comprising a braided tube, it should be understood that the tubular member may have a variety of suitable configurations.

Figure 2:
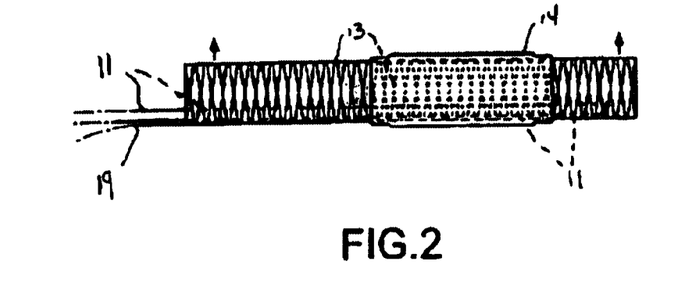
FIG. 2 is an enlarged view, partially in phantom, of a distal section of the catheter shown in FIG. 1, with the tubular member in the expanded configuration.

FIG. 2 illustrates the tubular member 13 in the expanded configuration after retraction of the pull line 19. As best illustrated in FIG. 2, showing the distal section of the shaft 11 within the inner lumen of the tubular member 13 in dotted phantom lines, the distal end of the shaft 11 is located proximal to the distal end of the expanded tubular member 13. In the embodiment illustrated in FIG. 2, the balloon 14 is in a nonexpanded configuration. The section of the tubular member under the balloon is illustrated in dashed phantom lines.

Figure 3:
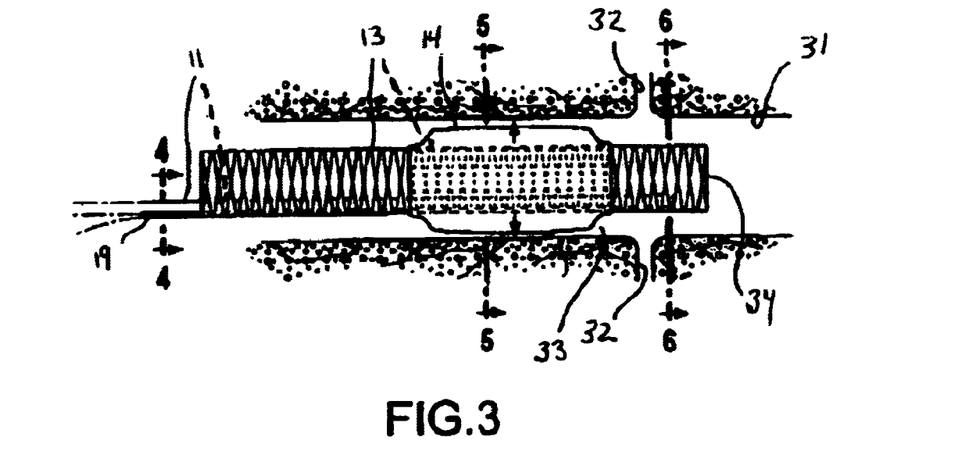
FIG. 3 is an enlarged view, partially in phantom, of a distal section of the catheter shown in FIG. 2, illustrating the catheter in the patient's descending aorta proximate the renal arteries, with the balloon in the inflated configuration.
Figure 4:
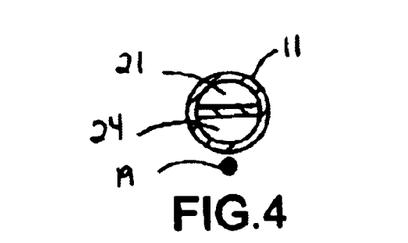
FIG. 4 is a transverse cross sectional view of the balloon shown in FIG. 3, taken along line 4—4.
Figure 5:
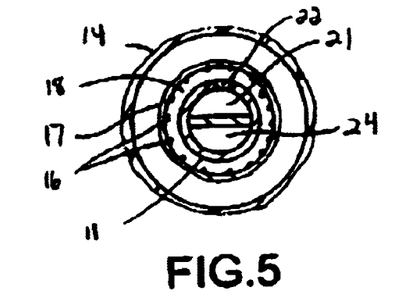
FIG. 5 is a transverse cross sectional view of the balloon shown in FIG. 3, taken along line 5—5.
Figure 6:
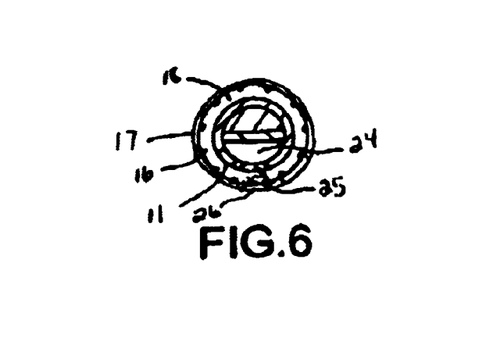
FIG. 6 is a transverse cross sectional view of the balloon shown in FIG. 3, taken along line 6—6.

FIG. 3 illustrates the catheter 10 with the balloon 14 in the expanded configuration. As best illustrated in FIGS. 4–6 showing transverse cross sections of the catheter shown in FIG. 3, taken along lines 4—4, 5—5, and 6—6, respectively, the shaft has an inflation lumen 21 extending from the proximal end of the shaft 11 to an inflation port 22 (FIG. 5) located on the shaft distal section, in fluid communication with the interior of the balloon. Arm 23 on adapter 15 provides access to the inflation lumen 21, and is in fluid communication with a source of inflation fluid (not shown). The shaft also has an agent delivery lumen 24 extending from the proximal end to an agent delivery port 25 in the distal end of the shaft 11. Arm 26 on adapter 15 provides access to the agent delivery lumen 24, and is in fluid communication with an agent source (not shown). The tubular member sheath 17 has an agent delivery opening 26 adjacent to the shaft agent delivery port 25, for providing a pathway for agent delivery from the lumen 24 to exterior to the tubular member 13. In the illustrated embodiment, the inflation lumen 21 and agent delivery lumen 24 are side-by-side in a multilumen shaft 11, with inflation port 22 extending through a side wall of the shaft. However, a variety of suitable configurations may be used as are conventionally used in catheter shaft design including coaxial lumens in fluid communication with side ports or ports in the distal extremity of the shaft. The agent delivery port 25 is preferably in a side wall of the shaft 11 distal section in fluid communication with the agent delivery lumen 24, however, alternatively, the agent delivery port 25 may be in the distal end of the shaft 11.

FIG. 3 illustrates the catheter 10 in a blood vessel 31, such as a descending aorta, of a patient, having branch vessels 32, such as the renal arteries, opening therein. The catheter 10 is introduced and advanced within the patient's blood vessel 31 in the low profile, unexpanded configuration illustrated in FIG. 1. The agent delivery port 25 is positioned proximate to (up-stream or in line with) the one or more branch vessels 32, and the distal end of the tubular member is preferably up-stream of the one or more branch vessels 32. The tubular member is then expanded to the expanded configuration, and, preferably, thereafter the balloon 14 is radially expanded by directing inflation fluid into the balloon interior. Specifically, in one embodiment of a method of the invention for delivery of a therapeutic or diagnostic agent to one or more of a patient's kidneys, the catheter is introduced into the femoral artery, as for example by the Seldinger technique, preferably slidingly over a guidewire (not shown), and advanced into the descending aorta 31. Although not illustrated, the shaft may be provided with a separate guidewire lumen, or the catheter may be advanced over a guidewire in agent delivery lumen 24 adapted to slidingly receive a guidewire. Alternatively, the catheter 10 may be advanced without the use of a guidewire. The agent delivery port 25 is positioned proximate to one or both renal arteries 32, as illustrated in FIG. 3, and the tubular member 13 extends within the aorta 31 up-stream and down-stream of the renal arteries 32. The tubular member 13 is radially expanded by retracting pull line 19. The interior passageway 18 of the tubular member 13 separates blood flow through the blood vessel 31 into an outer blood flow stream 33 exterior to the tubular member 13, and in inner blood flow stream 34 within the interior passageway 18 of the tubular member 13. The balloon 14 is expanded by directing inflation fluid into the inflation lumen. In the embodiment illustrated in FIG. 3, the balloon 14 is expanded to an outer diameter which does not completely occlude the patient's aorta 31. However, in an alternative embodiment, the balloon expands into contact with the wall of the aorta 21, to an outer diameter which completely occludes the aorta 31 (not shown). Balloon 14 may have a length and elongated configuration configured to provide mechanical stability for and coaxial centering of the operative distal section of the catheter in the blood vessel 31. A stabilizing member (not shown) may be provided on an outer surface of the distal end of the tubular member 13, such as for example unfoldable arms which anchor the distal end of the catheter in the aorta 31 during delivery of agent. A variety of suitable imaging modalities may be used to position the catheter in the desired location in the blood vessel, such as fluoroscopy, or ultrasound. For example, radiopaque markers (not shown) on the shaft may be used in positioning the radially expandable member 14 and agent delivery port 25 at the desired location in the blood vessel 31.

A therapeutic or diagnostic agent (hereafter "agent") is delivered to the renal arteries 32 by introducing the agent into the agent delivery lumen 24 in the shaft 11, and out the agent delivery port 25. An agent delivery opening 26 in the tubular member 13 adjacent to the agent delivery port 25 provides a pathway for agent delivery from lumen 24 to external to the tubular member 13. The agent delivery port 25 is up-steam of the renal arteries 32 and proximal to the distal end of the tubular member 13. Thus, the outer blood flow stream 33 has a relatively high concentration of agent and the inner blood flow stream 34 has a relatively low concentration or no agent. Additionally, the balloon 14 in the expanded configuration restricts the flow of blood to decrease the blood flow exterior to the proximal portion of the tubular member 13 down-stream of the renal arteries 32 in comparison to the blood flow stream exterior to the distal portion of the tubular member 13 up-stream of the renal arteries 32. As a result, a relatively large amount of the agent delivered from the agent delivery port 25 is directed into the renal arteries 32, in comparison to the amount of agent which flows down-stream of the renal arteries 32 in the aorta 31.

In one embodiment, the outer blood flow stream is substantial. Preferably, the cross-sectional area of the inner lumen 18 of the tubular member 13 is about 4% to about 64% of the blood vessel 31 (i.e., aorta) cross-sectional area, or about 4 mm to about 16 mm for a blood vessel 31 having a 20 mm inner diameter. It should be noted that in some embodiments, the cross-sectional area of the wall of the tubular member 13 is not insignificant in relation to the cross-sectional area of the blood vessel 31. In the embodiment illustrated in FIG. 1 in which tubular member 13 comprises sheath 17 on a frame of filaments 16, this cross-sectional area is negligible. In alternative embodiments discussed below, such as the embodiments illustrated in FIGS. 10 and 13, the cross-sectional area of the wall of the tubular member 13 may be about 2% to about 50%, more specifically about 5% to about 20%, of the cross-sectional area of a section of the blood vessel 31 located at the up-stream most end of the catheter 10. Additionally, the aorta has multiple branch vessels in addition to the renal arteries which effect the total flow in the aorta at a given location therein. Thus, a percentage of the blood flow that enters the abdominal aorta, i.e., past the diaphragm, is delivered in the normal rest state of circulation to the celiac trunk, the superior and inferior mesenteric arteries, and the renal arteries. Nonetheless, the flow segmentation created by the presence of the deployed catheter 10 is such that the blood flow in the outer blood flow stream of a patient at rest is about 10% to about 90% of the total blood flow immediately up-stream of the up-stream or distal most end of the tubular member 13, i.e., of the total blood flow present in the section of the aorta immediately adjacent to the renal arteries. Similarly, the blood flow in the inner blood flow stream of a patient at rest is about 10% to about 90% of the total blood flow immediately upstream of the up-stream or distal most end of the tubular member 13. The flow in the outer blood flow stream is sufficient to provide adequate kidney function, although the flow required will vary depending upon factors such as the presence of drugs which increase flow or increase the ability of the tissue to withstand ischemic conditions.

While the renal arteries are illustrated directly across from one another in FIG. 3, and the method is discussed primarily in terms of delivery of agent to both renal arteries together, it should be understood that the catheter may be positioned and used to deliver agent to the renal arteries individually, and specifically in anatomies having the renal arteries longitudinally displaced from one another. The flow of agent is then stopped. The tubular member 13 is contracted by urging the pull line distally, and the balloon 14 is collapsed by removal of the inflation fluid, and the catheter removed from the patient.

Figure 7:
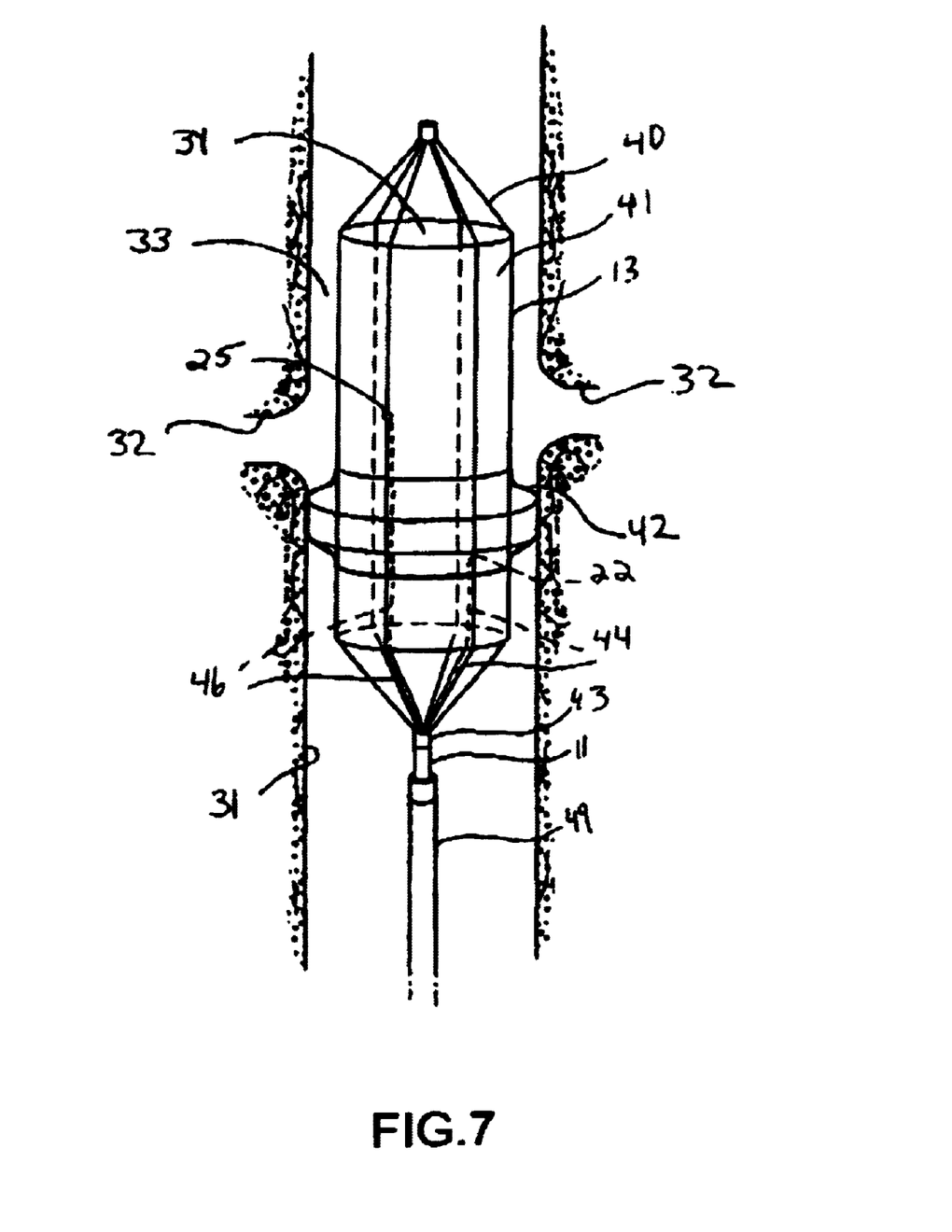
FIG. 7 is an enlarged view, partially in phantom, of a distal section of an alternative embodiment having an expandable tubular member comprising a sheath covered collapsible frame.

A variety of suitable radially expandable tubular members 13 may be used in the catheter 10 of the invention. FIG. 7 illustrates an alternative embodiment of distal end of the catheter 10 in which the tubular member 13 comprises a self-expanding frame 40 having a sheath 41 thereon. As discussed above in relation to the embodiment of FIG. 1, catheter shaft 11 defines an inflation lumen and an agent delivery lumen, and radially expandable member comprises a balloon 42 on an outer surface of sheath 41. For ease of illustration, the balloon 42 is shown as a transparent material. In the embodiment illustrated in FIG. 7, catheter shaft 11 comprises a multilumen proximal shaft 43 defining proximal sections of the inflation lumen 21 and agent delivery lumen 24, a first distal tubular member 44 defining a distal section of inflation lumen 21 extending to inflation port 22, and a second distal tubular member 46 defining a distal section of agent delivery lumen 24 extending to agent delivery port 25. First tubular member 44 extends distally from the distal end of the proximal section of the inflation lumen in the multilumen proximal shaft. Similarly, second tubular member 46 extends distally from the distal end of the proximal section of the agent delivery lumen in the multilumen proximal shaft. First and second tubular members 44146 are typically formed of thin-walled polymeric material such as polyimide, with an inner diameter of about 0.002 inch to about 0.006 inch, and a wall thickness of about 0.0005 inch and about 0.002 inch. In alternative embodiments, catheter shaft comprises an outer tubular member with first and second inner tubular members defining inflation lumen and agent delivery lumen, respectively, extending within the outer member and out the distal end thereof. The agent delivery lumen 24 extends to a location proximal to the distal end of the tubular member 13 and distal to the balloon. One or more agent delivery ports 25 are provided in a distal section of the agent delivery lumens, as discussed above in relation to the embodiment of FIG. 1. In alternative embodiments, one or more additional agent delivery lumens may be provided.

In the illustrated embodiment, the frame 40 comprises longitudinally extending filaments or struts, such as wires, joined together at the proximal and distal ends thereof. In a preferred embodiment, frame 40 is formed of high strength metal, such as stainless steel, nickel-titanium alloy, and titanium. However a variety of suitable materials can be used including rigid polymers. The filaments typically have a round transverse cross section, with a diameter of about 0.006 inch to about 0.016 inch, or a rectangular transverse cross section with a thickness of about 0.001 inch to about 0.006 inch and a width of about 0.006 inch to about 0.016 inch. Sheath 41 is similar to sheath 17 discussed in relation to the embodiment of FIG. 1, and is preferably a thin walled elastomeric tubular member. The tubular member 13 is illustrated in FIG. 7 in the expanded configuration. The frame 40 is radially collapsible to a low profile configuration with the sheath 41 in a folded or pleated compact configuration for advancement within the patient's blood vessel. Once in place at a desired location within the blood vessel, a restraining member which applies a radially compressive force, which holds the frame in the collapsed smaller diameter configuration, is removed so that the frame expands. The frame may be held in the collapsed smaller diameter configuration by a variety of suitable restraining members such as a delivery catheter or removable outer sheath. For example, in one embodiment, the frame is deformed into the smaller diameter configuration within the lumen of a delivery catheter 49, and then expanded in the blood vessel lumen by longitudinally displacing the frame out the distal end of the delivery catheter 49 to thereby remove the radially compressive force of the delivery catheter 49. Although not illustrated, a pull line similar to pull line 19 discussed above in relation to the embodiment of FIG. 1 may be provided to apply additional radially expanding force to the filaments to supplement their inherent spring force, and is preferably provided in the embodiments having a radially expandable member 14 comprising an inflatable balloon where inflation of the balloon creates a radially compressive force on the tubular member 13.

In the embodiment illustrated in FIG. 7, balloon 42 is inflated into contact with the aorta wall 31 to an outer diameter which completely occludes the outer blood flow stream downstream of the renal arteries 32. Thus, the outer blood flow stream is directed into the branch vessels 32. However, the balloon may be configured to inflate to an outer diameter which does not completely occlude the downstream outer blood flow stream, as discussed above in relation to the embodiment of FIG. 3.

Figure 8A:
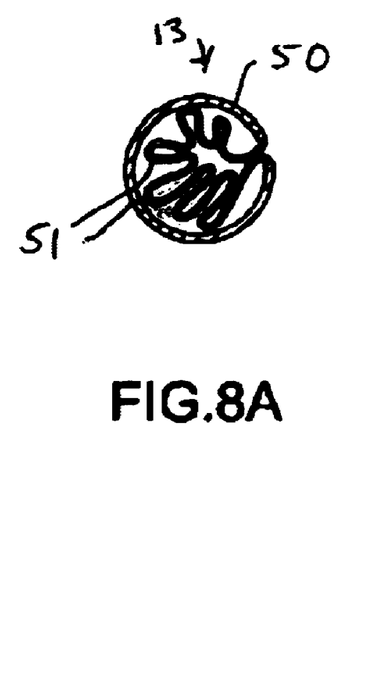
FIG. 8A is a transverse cross sectional view of an alternative embodiment having an expandable tubular member with a small profile wrapped configuration.
Figure 8B:
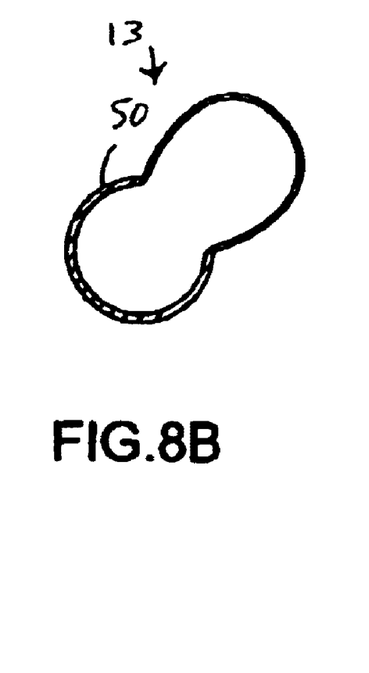
FIG. 8B is a transverse cross sectional view of the tubular member shown in FIG. 8A, illustrating the tubular member in the expanded unwrapped configuration.
Figure 9A:
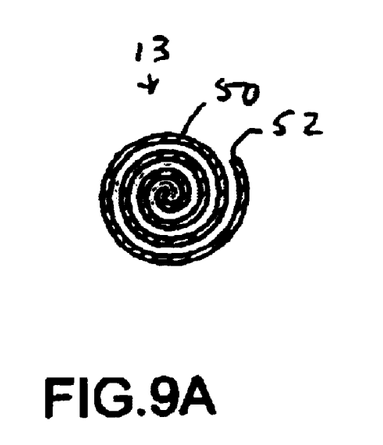
FIG. 9A is a transverse cross sectional view of an alternative embodiment having an expandable tubular member with a small profile wound configuration
Figure 9B:
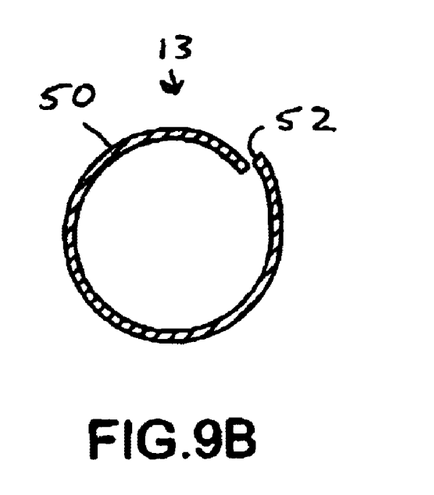
FIG. 9B is a transverse cross sectional view of the tubular member shown in FIG. 9A, illustrating the tubular member in the expanded unwound configuration.

FIGS. 8 and 9 illustrate transverse cross sectional views of an alternative embodiment in which the tubular member 13 comprises a sheet 50 configured to unwind from a wound low profile to an unwound radially expanded configuration to thereby radially expand the interior passageway 18 of the tubular member 13. FIG. 8A illustrates an embodiment in which the sheet 50 has a section wound back and forth into a plurality of folds 51. A restraining member (not shown) such as an outer sheath or delivery catheter is removed so that the sheet 50 unfolds as illustrated in FIG. 8B. The sheet section configured to be folded is preferably a thinner walled or otherwise more flexible than the section of the sheet which is not folded. In another embodiment illustrated in FIG. 9A, the sheet 50 is wound around itself into a rolled-up configuration having a free edge 52 extending the length of the sheet 50, which unrolls to the radially expanded configuration illustrated in FIG. 9B. A variety of suitable unfurling or uncoiling configurations may be used in a tubular member which is radially expandable in accordance with the invention including a rolled awning-type mechanism, and the like.

Figure 10:
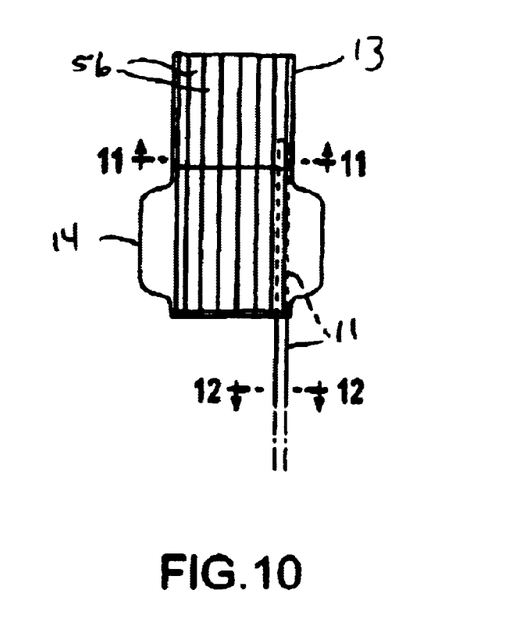
FIG. 10 illustrates an enlarged view of a distal section of an alternative embodiment having an expandable tubular member comprising a plurality of inflatable wall chambers or balloons secured together to form the tubular member.
Figure 16:
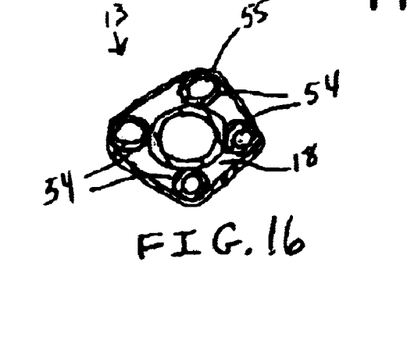
FIG. 16 is a transverse cross-sectional view of an alternative embodiment of an expandable tubular member comprising a plurality of inflatable balloons within an outer sheath.

FIG. 16 illustrates a transverse cross sectional view of an alternative embodiment in which the tubular member 13 comprises a plurality of inflatable balloons 54 within an outer sheath 55. The balloons 54 can be inflated from a noninflated low profile configuration to an inflated configuration. In the inflated configuration illustrated in FIG. 10, inner passageway 18 is defined between the inflated balloons in part by the sheath 55. Preferably, three or more balloons 54 are provided to in part define the inner passageway 18. Balloons 54 are preferably formed of a noncompliant material such as PET, or a complaint material such as polyethylene having reinforcing members such as wire members. Although four, cylindrical balloons 54 are illustrated in FIG. 10, it should be understood that a variety of suitable configurations may be used, including balloons having outer channels such as a spiraled balloon defining an outer spirally extending blood flow channel, similar in many respects to perfusion balloons for dilatation. An inflation lumen is provided in the catheter shaft 11 in fluid communication with balloons 54.

Figure 11:
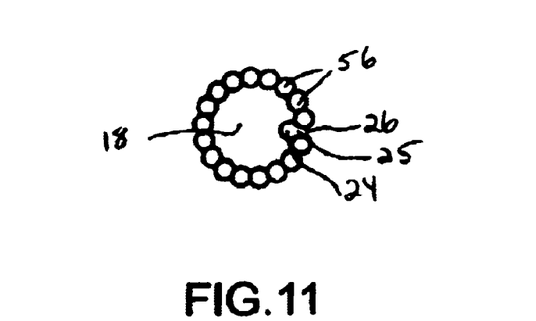
FIG. 11 is a transverse cross sectional view of the catheter shown in FIG. 10, taken along line 11—11.
Figure 12:
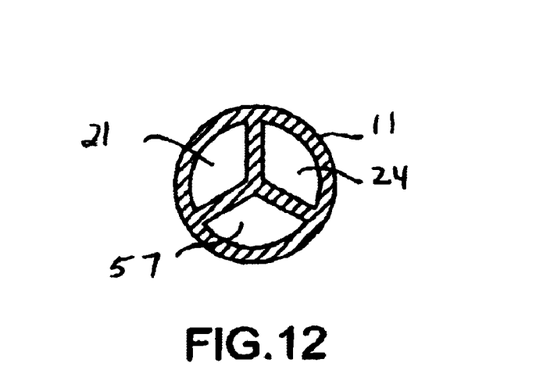
FIG. 12 is a transverse cross sectional view of the catheter shown in FIG. 10, taken along line 12—12.

FIGS. 10–12 illustrate an alternative embodiment in which tubular member 13 comprises a plurality of inflatable fluid-communicating wall chambers 56. In the embodiment of FIG. 10, the tubular member 13 comprises a plurality of tubular balloons joined together. For ease of illustration, the radially expandable member 14 which is an inflatable balloon is shown as a transparent material, As best illustrated in FIG. 11 showing a transverse cross sectional view of the tubular member 13 taken along line 11—11, each tubular balloon 56 is joined to adjacent balloons along a length thereof, to thereby define the tubular member interior passageway 18. As best illustrated in FIG. 12 showing a transverse cross sectional view of the catheter shaft 11 taken along line 12—12, the multilumen shaft 11 defines an inflation lumen 21 in fluid communication with balloon 14 on an outer surface of the tubular member 13, an agent delivery lumen 24 in fluid communication with agent delivery port 25, and a second inflation lumen 57 in fluid communication with the tubular balloons 56. Agent delivery opening 26 adjacent to the shaft agent delivery port 25 provides a pathway for agent delivery from the lumen 24 to exterior to the tubular member 13. The balloons 56 can be bonded together using a variety of suitable methods including as adhesive, heat fusion bonding, or solvent bonding such as with hexa-fluoro isopropanol (HFIP) for PET balloons. The tubular member 13 defined by the balloons 56 can be deflated and compressed, folded, pleated or otherwise reduced in size for introduction and advancement within the patient's blood vessel. In a presently preferred embodiment, the pressure required to inflate the balloon 14 is significantly lower than the pressure used to inflate the balloons 56 forming the tubular member 13, so that inflation of the balloon 14 does not deform the tubular member 13.

Figure 13:
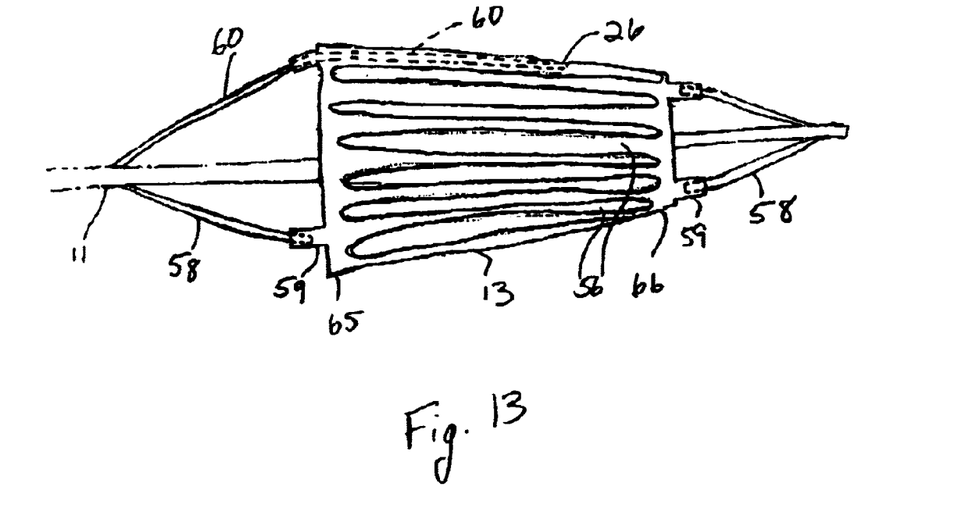
FIG. 13 illustrates an enlarged view of a distal section of an alternative embodiment having an expandable tubular member comprising a plurality of fluid-communicating wall chambers, wherein the tubular member has a conical shape.
Figure 14:
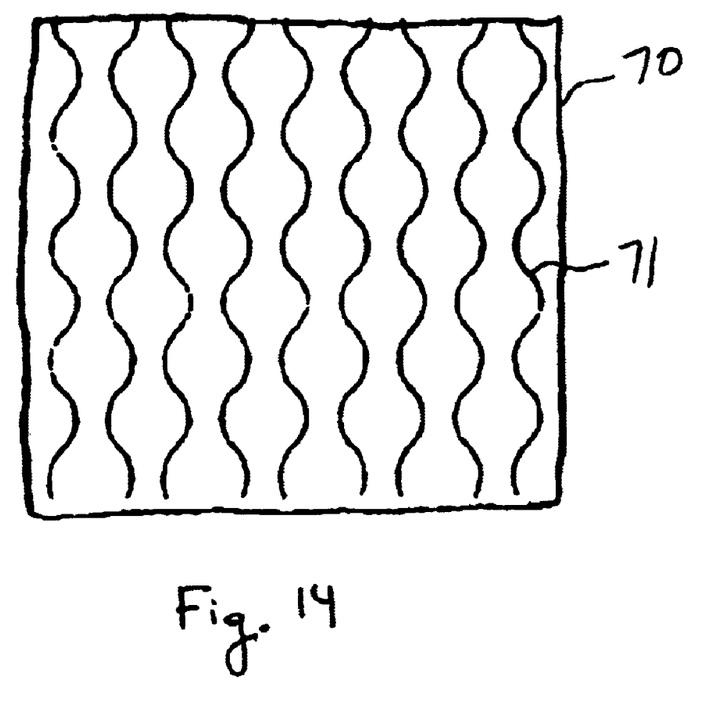
FIG. 14 is an elevational view of fused polymeric sheets used to form the tubular member, having curved seal lines forming the fluid-communicating chambers.

FIG. 13 illustrates an enlarged distal end of one embodiment having a tubular member 13 formed of a plurality of inflatable fluid-communicating wall chambers 56, in which one or more inflation tubes 58 extend from a port in the sidewall of shaft 11 in communication with inflation lumen 57 to the distal and/or proximal end of the tubular member. The inflation tubes 58 are in fluid communication with the wall chambers of the tubular member 13, and are used for delivering inflation fluid into the wall chambers 56 to thereby inflate the tubular member 13. In the embodiment of FIG. 13, the inflation tube 58 is secured to tubular member 13 by an adapting member or channel 59 at an end of the tubular member 13. One or more agent delivery tubes 60 extend from a port in the shaft 11 in fluid communication with agent delivery lumen 24 and into a wall chamber 56 of the tubular member 13. Agent delivery port 25 at the distal end of the agent delivery tube 60 extends to and in fluid communication with an agent delivery opening 26 in a wall defining a wall chamber of the tubular member 13. The section of the agent delivery tube 60 located within a wall chamber of the tubular member is illustrated in phantom in FIG. 13. Thus, one or more wall chambers of the tubular member can be used for agent delivery rather than inflation of the tubular member 13.

In the embodiment illustrated in FIG. 13, the tubular member 13 is conical. The conical tubular member 13 tapers from a large diameter down-stream end 65 to a smaller diameter up-stream end 66, so that the large diameter down-stream end 65 of the tubular member 13 forms the radially expandable member 14. Consequently, a separate radially expandable member 14 is not provided.

Figure 15:
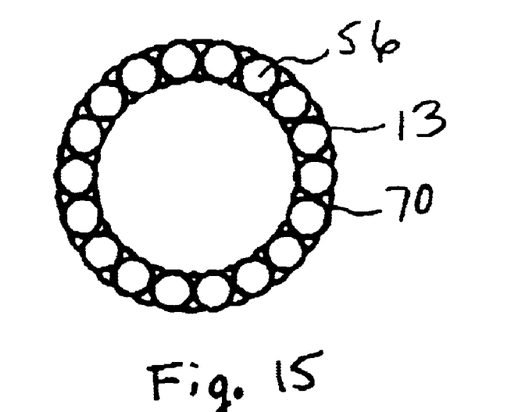
FIG. 15 is a transverse cross-sectional view of a tubular member formed of the sheets illustrated in FIG. 14.

The tubular member 13 comprising a plurality of inflatable fluid-communicating wall chambers 56 illustrated in FIG. 13 can be formed by heat sealing or fusing, as for example with a laser, two sheets of a polymeric film together with a plurality of longitudinally extending seal lines, so that each wall chamber is between adjacent seal lines. The seal lines forming the wall chambers do not extend to the proximal most and/or distal most end of the tubular member, so that the wall chambers are in fluid communication with one another. A variety of suitable materials can be used to form the sheets including polyolefins, low density polyethylene, polyurethane, polyamides, nylon, polyether block amide, polyethylene terephthalate, and other thermoplastics. The fused sheets are then wrapped into a cylindrical shape and the edges secured together to form a tubular member 13 which is collapsible and foldable into a compact configuration for advancement within the blood vessel. In the embodiments illustrated in FIGS. 10–13, the seal lines defining the wall chambers of the tubular member 13 extend in straight lines along a length of the tubular member. FIG. 15 illustrates an elevational view of fused sheets 70 for forming an alternative embodiment of a tubular member 13 in which the wall chambers 56 are defined by curvilinear seal lines 71 to form interleaved cells, so that a more complete occlusion is provided by the tubular member 13. FIG. 16 illustrates a transverse cross-sectional view of an expanded tubular member 13 formed from the curved seal lines.

Figure 17:
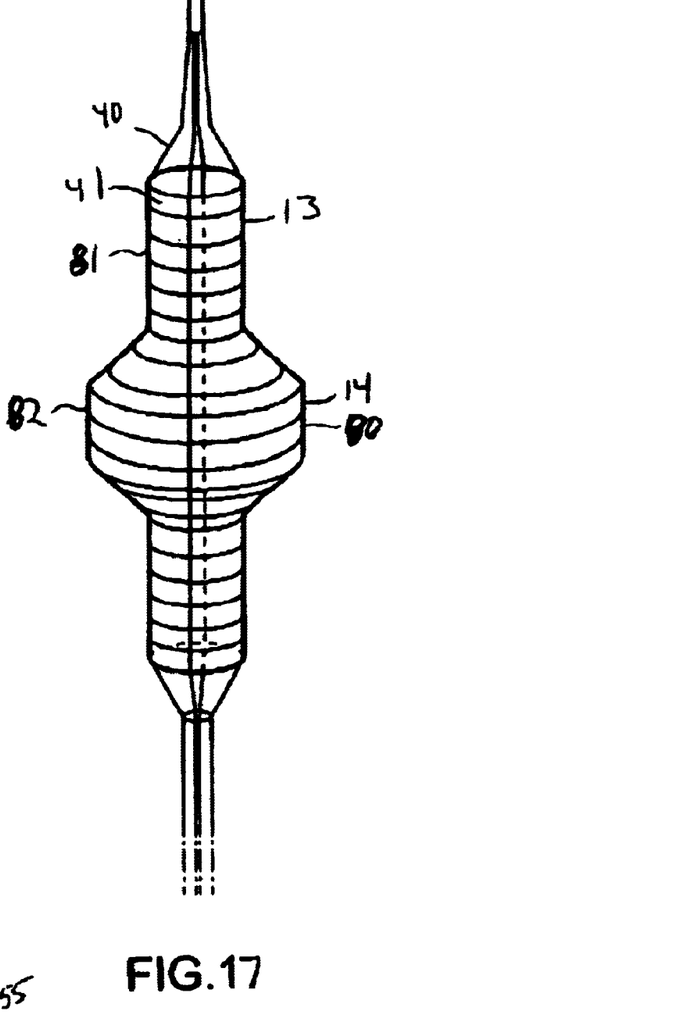
FIG. 17 is an enlarged view, partially in phantom, of a distal section of an alternative embodiment having a radially expandable member comprising a radially enlarged section of the expandable tubular member.

FIG. 17 illustrates an alternative embodiment similar to the embodiment shown in FIG. 7 except that the radially expandable member 14 comprises a radially enlarged section 80 of the tubular member 13. Thus, the frame 40, with sheath 41 thereon, forming the tubular member 13 does not have a uniform outer diameter, but instead radially expands from a collapsed configuration to define a smaller diameter section 81 defining tubular member 13, and a larger diameter section 82 defining the radially expandable member 14.

The dimensions of catheter 10 are determined largely by the size of the size of the blood vessel(s) through which the catheter must pass, and the size of the blood vessel in which the catheter is deployed. The length of the tubular member 13 is typically about 50 to about 150 mm, preferably about 80 to about 120 mm. The tubular member 13 has an unexpanded outer diameter of the tubular member is typically about 1 to about 5 mm, preferably about 2 to about 4 mm, and a radially expanded outer diameter of about 40 to about 140 mm, preferably about 60 to about 120 mm. The radially expanded interior passageway 18 of the tubular member 13 is typically about 30 to about 130 mm, preferably about 50 to about 110 mm to provide sufficient perfusion. The interior passageway 18 of the tubular member 13 has a radially expanded inner diameter which is about 1000% to about 6000% larger than the unexpanded inner diameter of the passageway 18. The radially expandable member 14 has a length of about 10 to about 50 mm, preferably about 20 to about 40 mm. The expanded outer diameter of the radially expandable member 14 is about 10 to about 35 mm, preferably about 15 to about 30 mm. In the embodiment having a conically shaped tubular member 13, the tubular member dimensions given above should be understood to refer to the distal most (i.e., up-stream) or smaller diameter end of the conical member, unless otherwise stated. Similarly, in the embodiment in which the radially expandable member 14 comprises the larger diameter end of a conically shaped tubular member, the radially expandable member dimensions should be understood to refer to the proximal most (i.e., down-stream) or larger diameter end of the conical member.

Typically, the shaft 11 has an outer diameter of about 1 to about 5 mm. The inflation lumen 21 has an inner diameter of about 0.02 to about 0.06 mm, and the agent delivery lumen has an inner diameter of about 0.01 to about 0.04 mm. The length of the catheter is about 40 to about 100 cm, preferably about 60 to about 90 cm.

The invention has been discussed in terms of certain preferred embodiments. One of skill in the art will recognize that various modifications may be made without departing from the scope of the invention. Although discussed primarily in terms of controlling blood flow to a branch vessel such as a renal artery of a blood vessel, it should be understood that the catheter of the invention could be used to deliver agent to branch vessels other than renal arteries, or to deliver to sites other than branch vessels, as for example where the catheter is used to deliver an agent to the wall defining the body lumen in which the catheter is positioned, such as a bile duct, ureter, and the like. Moreover, while certain features may be shown or discussed in relation to a particular embodiment, such individual features may be used on the various other embodiments of the invention.

What is claimed is:

1. A method of controlling blood flow to a plurality of renal arteries via their respective renal ostia at unique relative locations along an abdominal aorta in a patient, comprising:
   a) providing a catheter comprising
      i) an elongated shaft with a proximal end portion and a distal end portion that is adapted to be positioned at a location within the abdominal aorta associated with the renal ostia;
      ii) a tubular member on the distal end portion having an interior passageway which is radially expandable within the abdominal aorta at the location, and which is configured to extend within the abdominal aorta upstream and downstream of the renal ostia; and iii) a radially expandable member on the tubular member, having an expanded configuration with an outer diameter larger than an outer diameter of the tubular member and which is configured to decrease the blood flow in the outer blood flow stream downstream of the renal ostia;

b) advancing the distal end portion to the location within the patient's abdominal aorta, so that an upstream end of the tubular member is upstream of the renal ostia and the radially expandable member is downstream of the renal ostia;

c) expanding the tubular member to separate blood flow through the abdominal aorta into an outer blood flow stream exterior to the tubular member and an inner blood flow stream within the interior passageway of the tubular member; and d) expanding the radially expandable member to the expanded configuration to thereby decrease the blood flow in the outer blood flow stream downstream of the renal ostia.

2. The method of claim 1, further comprising:

expanding the radially expandable member into contact with a wall of the abdominal aorta to substantially occlude the outer blood flow stream downstream of the renal ostia.

3. The method of claim 1, further comprising:

expanding the radially expandable member to an outer diameter which does not completely occlude the outer blood flow stream downstream of the renal ostia.

4. The method of claim 1, wherein the catheter used according to the method further comprises:

a fluid agent delivery system that is adapted to couple to a source of fluid agent located externally of the patient and cooperating with the tubular member and radially expandable member so as to deliver a volume of the fluid agent from the source and into the outer blood flow stream.

5. The method of claim 4, wherein the fluid agent delivery system comprises:

at least one lumen extending along the elongated shaft and in fluid communication with a distal agent delivery port located along the distal end portion and a proximal agent delivery port located along the proximal end portion, and wherein the radially expandable member is downstream of the agent delivery port.

6. The method of claim 5, wherein the tubular member has an upstream end located upstream of the distal agent delivery port.

7. The method of claim 5, wherein the tubular member has a distal end located distal to the distal agent delivery port.

8. The method of claim 5, wherein the distal agent delivery port is a lateral port in a side wall of the shaft.

9. The method of claim 1, wherein the tubular member comprises a braided tube having a sheath.

10. The method of claim 1, wherein the catheter used according to the method further comprises:

a pull line having a distal end attached to the tubular member, and wherein the interior passageway of the tubular member is radially expanded by proximally retracting the pull line.

11. The method of claim 1, wherein the tubular member is self expanding.

12. The method of claim 11, wherein the tubular member comprises a radially collapsible frame having a sheath.

13. The method of claim 1, wherein the interior passageway of the tubular member has an expanded inner diameter of between about 30 mm to about 130 mm.

14. The method of claim 1, wherein the interior passageway of the tubular member has an unexpanded inner diameter configured to expand to an expanded inner diameter, wherein the expanded inner diameter is between about 1000% to about 6000% larger than the unexpanded inner diameter.

* * * * *